(12) United States Patent
Das et al.

(10) Patent No.: US 9,480,634 B2
(45) Date of Patent: Nov. 1, 2016

(54) COSMETIC COMPOSITIONS

(71) Applicant: The Procter & Gamble Company, Cincinnati, OH (US)

(72) Inventors: Sourav Das, Memphis, TN (US); Naohisa Yoshimi, Singapore (SG); Shuhei Tanaka, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/694,128

(22) Filed: Apr. 23, 2015

(65) Prior Publication Data

US 2015/0305994 A1 Oct. 29, 2015

Related U.S. Application Data

(60) Provisional application No. 61/982,883, filed on Apr. 23, 2014.

(51) Int. Cl.
| | | |
|---|---|---|
| *A61Q 19/02* | (2006.01) | |
| *A61K 8/02* | (2006.01) | |
| *A61K 8/34* | (2006.01) | |
| *A61K 8/44* | (2006.01) | |
| *A61K 8/49* | (2006.01) | |
| *G01N 33/50* | (2006.01) | |
| *A61K 8/37* | (2006.01) | |
| *A61K 8/67* | (2006.01) | |
| *A61Q 19/00* | (2006.01) | |

(52) U.S. Cl.
CPC .............. *A61K 8/345* (2013.01); *A61K 8/34* (2013.01); *A61K 8/375* (2013.01); *A61K 8/44* (2013.01); *A61K 8/442* (2013.01); *A61K 8/4926* (2013.01); *A61K 8/675* (2013.01); *A61Q 19/02* (2013.01); *G01N 33/5044* (2013.01); *A61K 2800/591* (2013.01); *A61K 2800/75* (2013.01); *A61Q 19/00* (2013.01); *G01N 2405/00* (2013.01); *G01N 2500/04* (2013.01); *G01N 2500/10* (2013.01)

(58) Field of Classification Search
CPC ...... A61Q 19/00; A61Q 19/02; A61K 8/345; A61K 8/347
USPC .......................................... 424/400; 514/356
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 5,621,012 A | 4/1997 | Schoenrock | |
| 7,270,805 B1 * | 9/2007 | Shore ...................... A61K 8/49 424/400 |
| 8,697,750 B2 | 4/2014 | Omura | |
| 2013/0302391 A1 | 11/2013 | Kuromiya | |
| 2014/0036285 A1 | 2/2014 | Yamakawa | |
| 2014/0328775 A1 | 11/2014 | Laughlin, II | |

FOREIGN PATENT DOCUMENTS

| | | |
|---|---|---|
| DE | 4420625 C1 | 11/1995 |
| EP | 0769291 A1 | 4/1997 |
| EP | 2583663 A1 | 4/2013 |
| WO | WO2012/101102 A2 | 8/2012 |
| WO | WO2013/158824 A2 | 10/2013 |

OTHER PUBLICATIONS

International Search Report PCT/US2015/026737; Mailing Date Aug. 24, 2015; 13 pages.
Database GNPD [Online] MINTEL; Dec. 31, 2002 "Isoceance Age-Defence Physio Cream".

* cited by examiner

*Primary Examiner* — Kamal Saeed
*Assistant Examiner* — Janet L Coppins
(74) *Attorney, Agent, or Firm* — S. Robert Chuey

(57) ABSTRACT

A cosmetic composition comprising a safe and effective amount of a skin care active; a safe and effective amount of a skin lightening agent; a safe and effective amount of bisabolol; and a safe and effective amount of a glycerol ether of aliphatic alcohol, wherein the ratio of bisabolol to glycerol ether of aliphatic alcohol is from 2:1 to 1:15.

12 Claims, No Drawings

COSMETIC COMPOSITIONS

FIELD OF THE INVENTION

The present disclosure generally relates to a method of reducing irritability of skin care actives in a cosmetic composition comprising a glycerol ether of aliphatic alcohol and bisabolol, and to cosmetic compositions relating thereto.

BACKGROUND OF THE INVENTION

Consumers often desire skin lightening products that are affordable, safe, stable, and can produce consumer-noticeable skin lightening after routine use. In this regard, consumers may desire skin lightening products to either lighten the color of their skin and/or minimize skin spots or blotchiness. For example, consumers may desire skin lightening agents to counteract fluctuations in skin color brought about by hormonal fluctuations or environmental stressors like UV light.

At least some skin lightening agents work by targeting or influencing one or more of the steps involved in the development of skin color. Human skin color is attributed in part to the outermost layer of skin (i.e. epidermis) where many melanocytes may be located. The synthesis of melanin, pigments that may be dark brown/black or light red-yellow, is a complex process that involves the enzyme, tyrosinase, and can take place within the melanosomes of the melanocytes. These melanosomes may be transferred from the melanocyte to the keratinocytes.

It has been discovered that combining different skin lightening agents, for example—combining vitamin B3 with N-undecylenoyl-L-phenylalanine, can increase their effectiveness. However, combining ingredients may also result in undesirable side-effects, such as increased irritation and/or erythema, on certain skin-types dependent, for example, on the conditions in which the topical composition is applied. Consumers experiencing a level of discomfort and/or irritability upon using a cosmetic composition including skin lightening products may choose not to repurchase said cosmetic composition. Thus, there exists a need to find a solution to reduce negative effects, such as irritation, while maintaining an acceptable level of efficacy of skin lightening.

SUMMARY OF THE INVENTION

A cosmetic composition suitable for topical application is provided. A cosmetic composition, comprising a safe and effective amount of a first skin care active; a safe and effective amount of a skin lightening agent; a safe and effective amount of bisabolol; and a safe and effective amount of a glycerol ether of aliphatic alcohol is provided, wherein the ratio of bisabolol to glycerol ether is from 2:1 to 1:15.

A method of reducing irritability of a skin care composition comprising a first skin care active and a skin lightening agent is provided. The method comprises the steps of: a) identifying that said cosmetic composition causes irritation in at least one human subject when said cosmetic composition is applied to keratinous tissue; and b) adding to said cosmetic composition bisabolol and glycerol ethers of aliphatic alcohols at a ratio of between 2:1 and 1:15 of bisabolol to glycerol ether to mitigate said irritation.

DETAILED DESCRIPTION OF THE INVENTION

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Cosmetic composition" as used herein, means compositions suitable for topical application on mammalian keratinous tissue.

"Derivatives" as used herein, includes but is not limited to, amide, ether, ester, amino, carboxyl, acetyl, and/or alcohol derivatives of a given compound.

"Diluent" as used herein, includes a material in which compounds (e.g. a skin care active or skin lightening agent) can be dispersed, dissolved, or otherwise incorporated.

"Hyperpigmentation" as used herein, refers to an area of skin wherein the pigmentation is greater than that of an adjacent area of skin (e.g., a pigment spot, an age spot, and the like).

"Keratinous tissue" as used herein, refers to keratin-containing layers disposed as the outermost protective covering of mammals which includes, but is not limited to, skin, hair, nails, cuticles, etc.

"Safe and effective amount" as used herein, means an amount sufficient to induce one or more biological effects, but low enough to avoid serious side effect, (e.g. undue toxicity or allergic reaction).

"Salts" as used herein, includes but is not limited to sodium, potassium, calcium, ammonium, manganese, copper, and/or magnesium salts of a given compound.

"Skin care actives" as used herein, means compounds that, when applied to the skin, provide a benefit or improvement to the skin. It is to be understood that skin care actives are useful not only for application to skin, but also to hair, nails and other mammalian keratinous tissue.

"Skin lightening agent" or "skin whitening agent" as used herein, are the same and include lightening of spots on skin (e.g. age spots and freckles). Skin lightening agents are a sub-set of skin care actives and include compounds that, when applied to skin, result in physical and/or biological whitening, for example by reducing melanin production.

It has been discovered that combining skin care actives with other skin care actives, for example skin lightening agents, can improve efficacy of the active(s). For example, in the case of skin lightening, it is known that combining niacinamide with N-undecylenoyl-L-phenylalanine is more efficacious than using either of these skin actives individually. Niacinamide is a well known skin care active. N-undecylenoyl-L-phenylalanine is known to act as a penetration enhancer but is also known as a skin care active specifically targeting skin-lightening. While the increase in efficacy from combining niacinamide and N-undecylenoyl-L-phenylalanine is highly desirable, the combination sometimes leads to an increase in irritation, in the form of increased redness and erythema, suffered by certain users. Bisabolol is known to reduce inflammation and signs of redness. However, it has now surprisingly been discovered that a combination of bisabolol and glycerol ethers of aliphatic alcohol at a specific ratio acts synergistically to reduce irritation caused by the combination of niacinamide and N-undecylenoyl-L-phenylalanine.

Cosmetic Compositions

A cosmetic composition of the present invention may be applied to mammalian keratinous tissue, in particular to human skin. The cosmetic compositions may take various forms. For example, some non-limiting examples of forms include solutions, suspensions, lotions, creams, gels, toners, sticks, pencils, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

Cosmetic compositions may include a first skin care active such as a vitamin B compound. As used herein, vitamin B compounds include B1 compounds, B2 compounds, B3 compounds such as niacinamide, B5 compounds, such as panthenol or "pro-B5", pantothenic acid, pantothenyl, B6 compounds, such as pyroxidine, pyridoxal, pyridoxamine, carnitine, thiamine, and riboflavin. In some embodiments, the vitamin B compound is a B3 compound having the formula:

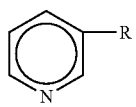

wherein R is —CONH2 (i.e., niacinamide), —COOH (i.e., nicotinic acid) or —CH2OH (i.e., nicotinyl alcohol); derivatives thereof; and salts of any of the foregoing. In some examples, the cosmetic compositions may have a concentration of a vitamin B compound, by weight of the cosmetic composition, of greater than 0.0005%, 0.00056%, 1%, 2%, 3%, 4%, or 5% and/or less than 11%, 10%, 8%, or 6%.

Cosmetic compositions may also include skin lightening agents. The skin lightening agent may be any known lightening agent, for example hydroquinone, ascorbic acid and derivatives, vitamin E and derivatives, resorcinols azelaic acid, butyl hydroxyanisole, gallic acid and its derivatives, ellagic acid, glycyrrhizinic acid, glycyrrhetinic acid, hydroquinone, kojic acid, arbutin, deoxyarbutin, mulberry extract, glucosamine, N-acetyl glucosamine, tunicamycin, protease inhibitors, retinoids, hydrocortisone, phytosterol, salicylic acid, rucinol, chamomile extract, linoleic acid, tranexamic acid, magnoligran, 4-(4-hydroxyphenyl)-2-butanol, and mixtures thereof. In specific embodiments, the skin lightening agent is an N-acyl amino acid, for example N-undecylenoyl-L-phenylalanine, N-palmitoyl alanine, N-palmitoyl glycine, N-palmitoyl isoleucine and N-cocoyl alanine, N-lauroyl-L-phenylalanine, N-caproyl-L-phenylalanine, N-myristoyl-L-phenylalanine. Preferably, the skin lightening agent is N-undecylenoyl-L-phenylalanine, which is commercially available from SEPPIC® and sold under the name of Sepiwhite®. In some examples, the cosmetic compositions may include from 0.0001%, 0.001%, 0.01% to about 1%, 2%, 3% or 5% of N-undecylenoyl-L-phenylalanine, by weight of the cosmetic composition.

N-undecylenoyl-L-phenylalanine possesses the following formula:

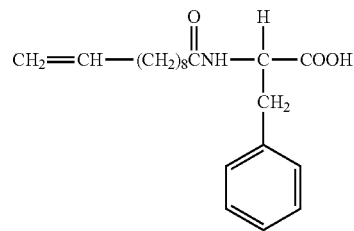

Cosmetic compositions may also include bisabolol. Bisabolol has previously been used as a fragrance ingredient in consumer products like fine fragrances, shampoos, soaps, and cosmetics.

Bisabolol may be naturally- or synthetically-derived, or may include a mixture of natural and synthetic origin. Bisabolol may be added to the composition, for example, in pure form, as a salt, as an extract, or in any other form. Bisabolol includes, for example, "alpha-bisabolol," which includes (+)-alpha-bisabolol, (−)-alpha-bisabolol, (+)-epi-alpha-bisablol, (−)-epi-alpha-bisablol, and combinations thereof. In some examples, the cosmetic compositions may include from 0.0001%, 0.001% or 0.005% to 0.01%, 0.1% or 0.2% of bisabolol, by weight of the cosmetic composition.

Bisabolol possesses the following formula:

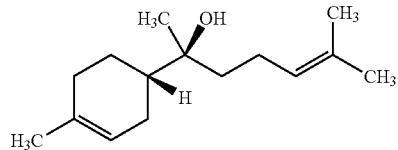 [SMILES: CC(C)=CCC[C@](C)(O)[C@@H]1CC=C(C)CC1]

The cosmetic compositions may include glycerol ethers of saturated and/or unsaturated, branched and/or unbranched aliphatic alcohols having 12 to 24 carbon atoms. Examples of glycerol ethers of saturated and/or unsaturated branched and/or unbranched aliphatic alcohols having 12 to 24 carbon atoms are:

Batyl alcohol, having the following formula:

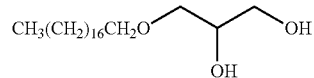

Chimyl alcohol with the following formula:

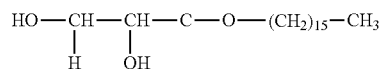

Selachyl alcohol with the following formula:

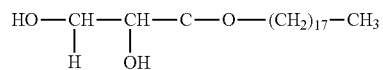

In some examples, the cosmetic composition may comprise from about 0.001%, 0.01%, 0.1%, 0.5% or 1% to about 2%, 3%, 4%, 5% or 10% of a glycerol ether, by weight of the cosmetic composition.

In examples, the cosmetic composition includes a ratio of bisabolol to glycerol ether of from about 2:1, 1:1, 1:2, 1:2.5 to 1:5, 1:10 or 1:15.

The topical application of niacinamide may be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. Thus, in certain instances, it may be desirable to include niacinamide in the cosmetic composition in order to improve the appearance of aging/photo-damaged skin.

The cosmetic compositions may also comprise one or more humectants. Some non-limiting examples of humectants include sorbitol, honey, propylene glycol, and glycerin. Glycerin, for example, is a small, polar molecule that is liquid at room temperature and miscible with water. Endogenous glycerin is believed to be an important component of skin hydration and topical application of cosmetic products containing glycerin can be associated with improvements in barrier function, induction of biomarkers associated with keratinocyte proliferation and wound healing, reduction in melanin intensity, increases in epidermal thickness, and improvements in general skin appearance.

The cosmetic compositions may also comprise a dermatologically acceptable carrier (which may also be referred to as a "carrier") within which the vitamin B3 compound, and the N-undecylenoyl-L-phenylalanine compound are incorporated to enable the compounds and optional other ingredients to be delivered to the skin. The carrier may contain one or more dermatologically acceptable solid, semi-solid or liquid fillers, diluents, solvents, extenders components, materials and the like. The carrier may be solid, semi-solid or liquid. The carrier may be provided in a wide variety of forms. Some non-limiting examples include simple solutions, (aqueous or oil based), emulsions, and solid forms (e.g., gels, sticks, flowable solids, amorphous materials).

The carriers may contain one or more dermatologically acceptable, hydrophilic diluents. Hydrophilic diluents include water, organic hydrophilic diluents such as lower monovalent alcohols (e.g., C1-C4) and low molecular weight glycols and polyols, including propylene glycol, polyethylene glycol (e.g., molecular weight 200-600 g/mole), polypropylene glycol (e.g., molecular weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Carriers may also be in the form of an emulsion, such as oil-in-water emulsions, water-in-oil emulsions, and water-in-silicone emulsions. An emulsion may generally be classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. The aqueous phase may comprise water, such as a solution as described above. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. Emulsions may also contain from about 1% to about 10% or from about 2% to about 5%, of an emulsifier, based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986), each incorporated herein by reference.

A wide variety of optional components/ingredients may be included in the cosmetic compositions. For example, the cosmetic compositions may include absorbents, abrasives, anti-caking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993).

Various cosmetic treatments may be employed for use on different skin surfaces. Skin surfaces of particular interest are those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the cosmetic compositions described herein.

The treatment method may include applying the cosmetic composition to a previously identified area of skin in need of treatment, or an area where one seeks to prevent, treat or reduce the appearance of age spots and/or improve skin tone evenness. Many regimens exist for the application of the cosmetic composition. The cosmetic composition may be applied at least once a day, twice a day, or on a more frequent daily basis, during a treatment period. When applied twice daily, the first and second applications are separated by at least 1 to 12 hours. Typically, the cosmetic composition may be applied in the morning and/or in the evening before bed.

The treatment period is ideally of sufficient time to provide an improvement in the appearance of the age spots or skin tone evenness. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the cosmetic composition is applied at least once a day during a treatment period of at least 4 weeks, 8 weeks, or 12 weeks. In one embodiment the cosmetic composition is applied twice a day during a treatment period of at least 4 weeks, 8 weeks, or 12 weeks.

A method of reducing the irritability of a cosmetic composition as described above is also provided. The method may include the steps of identifying that a cosmetic composition including a skin care active and a skin lightening agent causes irritation in at least one human subject when said cosmetic composition is applied to keratinous tissue, and adding to the cosmetic composition bisabolol and glycerol ethers of aliphatic alcohols at a ratio of from 2:1 to 1:15 (bisabolol to glycerol ether) to mitigate the irritation. In a specific embodiment, skin irritancy is measured using a PGE-2 assay (described below).

PGE-2 Assay

Redness and swelling upon application of a material or combination of materials in skin is associated with an increase in generation of inflammatory mediators such as the Prostaglandin E2 (PGE2) mediator. Measuring the amount of PGE2 generation in keratinocytes in-vitro upon application of a material can give us an estimate whether a material or a combination of materials is likely to result in skin irritancy when applied on skin, as described in further detail in WO 93/17336.

The following method is used to estimate the generation of PGE2 in-vitro: Tert-keratinocytes are cultured until they reach a confluency of ~80%. Niacinamide, N-undecylenoyl-L-phenylalanine, bisabolol, and batyl alcohol were added (in the respective amounts shown in Tables 1 and 2) to understand the effect of each material on PGE2 generation. Arachidonic acid was also included in the treatment media for all samples as a substrate to form PGE2. The treated cells were further cultured overnight with the supernatants harvested for PGE2 quantitation using a homogeneous time resolved fluorescence (HTRF) technology system (Manufacturer CisBio®). The cells were assayed for ATP using the Cell Titer Glo system (Promega®). PGE2 release was normalized to ATP. PGE2 amount measured upon addition of materials was compared to the baseline in which no chemical was added (culture media only).

EXAMPLES

The examples provided in this application are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Table 1 below illustrates the effect of different test conditions on skin irritancy using the inflammatory mediator prostaglandin E2 (PGE2) assay disclosed herein. Comparing Example 2 to Example 1 (the control), a significant increase in PGE2 score can be seen—indicating a significant increase in skin irritancy. Thus, it can be seen that inclusion of both niacinamide and N-undecylenoyl-L-phenylalanine increases skin irritancy. Comparing Examples 3 and 4 with Example 2, it can be seen that there is a decrease in PGE2 marker, illustrating that inclusion of one of bisabolol or batyl alcohol can reduce skin irritancy caused by niacinamide and N-undecylenoyl-L-phenylalanine. Although there is a decrease in PGE2 marker in Examples 3 and 4, there is still an increase in skin irritancy vs Example 1. Comparing Example 5 with Example 2, it can be seen that there is a significant decrease in PGE2 marker, reducing the PGE2 marker below the control PGE2 level of Example 1. Furthermore, the magnitude of decrease of PGE2 marker for Example 5 vs Example 2 is more than the sum of the decreases in PGE2 score when comparing Examples 3 and 4 with Example 2.

Thus, it can be seen that inclusion of bisabolol and batyl alcohol results in a synergistic decrease in skin irritancy caused by the combination of niacinamide and undecylenoyl phenylalanine.

TABLE 1

| Example | Niacinamide (%) | N-undecylenoyl-L-phenylalanine (%) | Batyl Alcohol (%) | Bisabolol (%) | Average PGE2 count | Std. Dev. | p-value vs Sample 2 |
|---|---|---|---|---|---|---|---|
| 1 (control) | 0 | 0 | 0 | 0 | 907.8 | 347.3 | 0.022 |
| 2 | 0.0015 | 0.00032 | 0 | 0 | 1345.0 | 195.4 | 1 |
| 3 | 0.0015 | 0.00032 | 0 | 0.0001% | 1157.6 | 152.6 | 0.093 |
| 4 | 0.0015 | 0.00032 | 0.001 | 0 | 1268.7 | 165.6 | 0.482 |
| 5 | 0.0015 | 0.00032 | 0.001 | 0.0001% | 739.0 | 130.9 | 8.79E−05 |

Furthermore, it has surprisingly been found that the ratio of bisabolol to batyl alcohol present has a significant impact on reduction of skin irritancy as measured using the PGE2 assay, as illustrated in Table 2 below. The same levels of niacinamide and N-undecylenoyl-L-phenylalanine are used in each sample shown in Table 2 (0.0015% niacinamide; 0.00032% N-undecylenoyl-L-phenylalanine)—only the respective quantities of bisabolol to batyl alcohol have been modified.

TABLE 2

| Example | Niacinamide (%) | N-undecylenoyl-L-phenylalanine (%) | Bisabolol (%) | Batyl Alcohol (%) | Average PGE2 count | Std. Dev. | p-value vs Sample 2 |
|---|---|---|---|---|---|---|---|
| 6 | 0 | 0 | 0 | 0 | 0 | 0 | 2695 |
| 7 | 0.0015% | 0.00032% | 0 | 0 | 0 | 0 | 3690 |
| 8 | 0.0015% | 0.00032% | 2E−05 | 0.0005 | 25 | 1 | 3147 |
| 9 | 0.0015% | 0.00032% | 0.0002 | 0.002 | 10 | 1 | 2631 |
| 10 | 0.0015% | 0.00032% | 0.0002 | 0.001 | 5 | 1 | 2426 |
| 11 | 0.0015% | 0.00032% | 0.0002 | 0.0005 | 2.5 | 1 | 1783 |
| 12 | 0.0015% | 0.00032% | 0.0002 | 0.0003 | 1.5 | 1 | 2477 |
| 13 | 0.0015% | 0.00032% | 0.0002 | 0.0001 | 1 | 2 | 2696 |
| 14 | 0.0015% | 0.00032% | 0.002 | 0.0001 | 1 | 20 | 17150 |

Comparing Examples 9, 10, 11, 12 and 13 with Example 7, it can be seen that there is a significant decrease in PGE2 score, in all cases bringing the PGE2 level down to or below the PGE2 level of Example 6. Looking specifically at Example 11, which includes a ratio of 1:2.5 bisabolol to batyl alcohol, it can be seen that the PGE2 level drops significantly below the control PGE2 level. By contrast, looking at Example 8 that has a ratio of 1:25 (bisabolol to batyl alcohol), there is only a marginal decrease in PGE2 level vs Example 7, that includes only niacinamide and undecylenoyl phenylalanine. Looking at Examples 13 and 14, Example 13 that includes bisabolol and batyl alcohol at a ratio of 2:1 shows a significant decrease in PGE2 marker back to the base level of Example 6. By comparison, Example 14 that includes a ratio of 25:1 shows an increase in PGE2 level vs the control Examples 7 or 6. Accordingly, simply increasing the quantity of bisabolol in the formula is likely to lead to an increase in skin irritancy.

From the results shown in Table 2, it can clearly be seen that the respective volumes of bisabolol and batyl alcohol have an impact on the level of skin irritancy measured by the PGE2 assay and, in particular, a ratio of between about 2:1 (bisabolol:batyl alcohol) to 1:15 is preferred.

Examples of cosmetic compositions of the present invention are provided below.

| Component | Example 15 | Example 16 | Example 17 | Example 18 | Example 19 |
|---|---|---|---|---|---|
| Water | QS | QS | QS | QS | QS |
| Glycerin | 10 | 10 | 10 | 10 | 10 |
| Disodium EDTA | 0.1 | 0.1 | 0.1 | 0.1 | 0.1 |
| Undeclenoyl Phenylalanine | 2 | 0.2 | 1 | 1 | 1 |
| Triethanolamine | 0.7 | 0.07 | 0.35 | 0.35 | 0.35 |
| Bisabolol | 2 | 0.1 | 0.1 | 0.1 | 0.1 |
| Oils | 5.50 | 5.50 | 5.50 | 5.50 | 5.50 |
| Hexyldecanol | 5 | 0.05 | 5 | 0.05 | 5 |
| Powder | 0.25 | 0.25 | 0.25 | 0.25 | 0.25 |
| Emulsifiers | 0.5 | 0.5 | 0.5 | 0.5 | 0.5 |
| Preservatives | 0.55 | 0.55 | 0.55 | 0.55 | 0.55 |
| Fatty Alcohols | 2.0 | 2.0 | 2.0 | 2.0 | 2.0 |
| Polymer Thickener | 2.25 | 2.5 | 2.25 | 2.25 | 2.5 |
| Panthenol | 1 | 1 | 1 | 1 | 1 |
| Niacinamide | 5 | 5 | 5 | 5 | 0 |
| Dimethicone and Dimethiconol | 2 | 2 | 2 | 2 | 2 |
| Batyl Alcohol | 2 | 0.5 | 1 | 0.5 | 0.5 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing the irritability of a cosmetic composition comprising a first skin care active and a skin lightening agent, the method comprising the steps of:
    a) identifying that said cosmetic composition causes irritation in at least one human subject when said cosmetic composition is applied to keratinous tissue comprising a step of determining the irritability of said cosmetic composition by measuring PGE2 levels in a PGE2 assay; and
    b) adding to said cosmetic composition bisabolol and glycerol ethers of aliphatic alcohols at a ratio of between 2:1 and 1:15 of bisabolol to glycerol ether to mitigate said irritation.

2. A method of reducing the irritability of a cosmetic composition as claimed in claim 1, wherein the glycerol ether of aliphatic alcohol has a carbon chain length of between 12 and 24.

3. A method of reducing the irritability of a cosmetic composition as claimed in claim 1, wherein the glycerol ether of aliphatic alcohol is batyl alcohol.

4. A method of reducing the irritability of a cosmetic composition as claimed in claim 1, wherein the cosmetic composition comprises no greater than 0.2% by weight of the composition of bisabolol.

5. A method of reducing the irritability of a cosmetic composition as claimed in claim 1, wherein the ratio of bisabolol to glycerol ether is at least 1:1.5.

6. A method of reducing the irritability of a cosmetic composition as claimed in claim 1, wherein the skin care active is vitamin B3 or a derivative thereof.

7. A method of reducing the irritability of a cosmetic composition as claimed in claim 1, wherein the skin care active is niacinamide.

8. A method of reducing the irritability of a cosmetic composition as claimed in claim 1, wherein the skin lightening agent is an N-acyl amino acid.

9. A method of reducing the irritability of a cosmetic composition as claimed in claim 1, wherein the skin lightening agent is N-undecylenoyl-L-phenylalanine.

10. A cosmetic composition for skin lightening with reduced irritability, comprising:
    a) a safe and effective amount of a skin care active;
    b) a safe and effective amount of a skin lightening agent;
    c) a safe and effective amount of bisabolol; and
    d) a safe and effective amount of batyl alcohol, chimyl alcohol or selachul alcohol, wherein the ratio of bisabolol to batyl alcohol, chimyl alcohol or selachul alcohol is from 2:1 to 1:15.

11. A cosmetic composition for skin lightening with reduced irritability, comprising:
    a) from about 0.0005% to about 11% by weight of the composition of a skin care active;
    b) from about 0.0001% to about 5% by weight of the composition of a skin lightening agent;
    c) from about 0.0001% to about 0.2% by weight of the composition of bisabolol; and
    d) from about 0.001% to of batyl alcohol, chimyl alcohol or selachul alcohol, wherein the ratio of bisabolol to batyl alcohol, chimyl alcohol or selachul alcohol is from 2:1 to 1:15.

12. A cosmetic composition, as claimed in claim 10 or 11, wherein the skin care active is a Vitamin B3 compound and the skin lightening agent is an N-acyl amino acid.

\* \* \* \* \*